US 9,241,677 B2

(12) United States Patent
Liao-Chen et al.

(10) Patent No.: US 9,241,677 B2
(45) Date of Patent: Jan. 26, 2016

(54) DEVICE AND METHODS FOR ASSESSING, DIAGNOSING, AND/OR MONITORING HEART HEALTH

(71) Applicant: MobHealth Corporation, El Monte, CA (US)

(72) Inventors: Kira Bingjie Liao-Chen, El Monte, CA (US); Jiali Lu, El Monte, CA (US); Fu Yu Li, Azusa, CA (US)

(73) Assignee: MOBHEALTH CORPORATION, El Monte, CA (US)

( * ) Notice: Subject to any disclaimer, the term of this patent is extended or adjusted under 35 U.S.C. 154(b) by 0 days.

(21) Appl. No.: 14/319,940

(22) Filed: Jun. 30, 2014

(65) Prior Publication Data

US 2015/0011904 A1    Jan. 8, 2015

Related U.S. Application Data

(60) Provisional application No. 61/842,307, filed on Jul. 2, 2013.

(51) Int. Cl.
| | |
|---|---|
| *A61B 5/04* | (2006.01) |
| *A61B 5/00* | (2006.01) |
| *A61B 5/044* | (2006.01) |
| *G06F 19/00* | (2011.01) |
| *A61B 6/00* | (2006.01) |

(52) U.S. Cl.
CPC .................. *A61B 5/742* (2013.01); *A61B 5/044* (2013.01); *G06F 19/3431* (2013.01); *G06F 19/3487* (2013.01); *A61B 6/503* (2013.01)

(58) Field of Classification Search
CPC ...... A61B 5/7275; A61B 5/0402; A61B 5/74; A61B 5/742; A61B 5/7405; A61B 5/021; A61B 6/503
See application file for complete search history.

(56) References Cited

U.S. PATENT DOCUMENTS

| | | | |
|---|---|---|---|
| 5,396,886 | A | 3/1995 | Cuypers |
| 6,285,898 | B1 | 9/2001 | Ben-haim |
| 6,656,126 | B2 | 12/2003 | Starobin |
| 6,768,919 | B2 | 7/2004 | Starobin |
| 7,308,309 | B1 | 12/2007 | Koh |
| 7,310,551 | B1 | 12/2007 | Koh |
| 7,381,536 | B2 | 6/2008 | Gurbel |
| 7,767,149 | B2 | 8/2010 | Maus |

(Continued)

FOREIGN PATENT DOCUMENTS

WO        0028460        5/2000

OTHER PUBLICATIONS

International Searching Authority at the U.S. Patent and Trademark Office, International Search Report and Written Opinion for PCT International Patent Application No. PCT/US2014/045133, Apr. 2, 2015, 8 pages.

*Primary Examiner* — Robert N Wieland
(74) *Attorney, Agent, or Firm* — Tucker Ellis LLP (57) ABSTRACT

A system for communicating heart health of an individual to the individual, comprises an input device useable to enter data relevant to the health of the individual an expert system including a knowledge base populated by a plurality of facts and rules for assessing heart health using the relevant data and an output device useable to communicate one or both of current heart health of the individual and a change in heart health that exceeds a threshold. At least some of the relevant data are biographical data and at least some of the relevant data are measurement data.

20 Claims, 13 Drawing Sheets

(56) References Cited

U.S. PATENT DOCUMENTS

| | | |
|---|---|---|
| 8,014,852 B2 | 9/2011 | Kwek |
| 8,041,417 B2 | 10/2011 | Jonckheere |
| 8,058,023 B2 | 11/2011 | Gurbel |
| 8,086,304 B2 | 12/2011 | Brockway |
| 8,175,895 B2 * | 5/2012 | Rosenfeld et al. ............ 705/3 |
| 8,219,186 B2 | 7/2012 | Chen |
| 8,229,551 B2 | 7/2012 | Xue |
| 8,392,053 B2 | 3/2013 | Gilbert |
| 8,409,104 B2 | 4/2013 | Cobain |
| 8,440,420 B2 | 5/2013 | Gurbel |
| 2006/0173307 A1 | 8/2006 | Amara |
| 2008/0076970 A1 | 3/2008 | Foulis |
| 2008/0160086 A1 | 7/2008 | Farber |
| 2009/0099468 A1 | 4/2009 | Thiagalingam |
| 2009/0227877 A1 | 9/2009 | Tran |
| 2009/0234406 A1 | 9/2009 | Shuros |
| 2011/0206794 A1 | 8/2011 | O'Kennedy |
| 2011/0251856 A1 | 10/2011 | Maus |
| 2011/0258049 A1 | 10/2011 | Ramer |
| 2011/0288419 A1 | 11/2011 | Baruch |
| 2012/0022350 A1 | 1/2012 | Teixeira |
| 2012/0029318 A1 | 2/2012 | Kuo |
| 2012/0089038 A1 | 4/2012 | Ryu |
| 2012/0215623 A1 | 8/2012 | Ramer |
| 2012/0216626 A1 | 8/2012 | Henry |
| 2012/0259233 A1 | 10/2012 | Chan |
| 2012/0265546 A1 | 10/2012 | Hwang |
| 2013/0018233 A1 | 1/2013 | Cinbis |
| 2013/0046153 A1 | 2/2013 | Hyde |
| 2013/0231947 A1 * | 9/2013 | Shusterman ............ 705/2 |
| 2013/0268016 A1 | 10/2013 | Xi |
| 2014/0106866 A1 | 4/2014 | Hardy |
| 2014/0142443 A1 | 5/2014 | Ngo |

* cited by examiner

DEVICE AND METHODS FOR ASSESSING, DIAGNOSING, AND/OR MONITORING HEART HEALTH

CROSS-REFERENCE TO RELATED APPLICATIONS

This application claims the benefit of U.S. Provisional Application No. 61/842,307, filed Jul. 2, 2014, the contents of which are incorporated herein by reference.

FIELD OF THE INVENTION

Embodiments of the present invention are related to a device and methods for assessing, diagnosing, and/or monitoring heart health of an individual.

BACKGROUND

According to the 2011 National Center for Health Statistics report, cardiovascular disease remains the leading cause of death in the United States in men and women of every major ethnic group. It accounted for nearly 616,000 deaths in 2008 and was responsible for 1 in 4 deaths in the U.S. in the same year. Coronary artery disease (CAD) is the most common type of heart disease and in 2008, 405,309 individuals died in the U.S. from this specific etiology. Every year, approximately 785,000 Americans suffer a first heart attack and another 470,000 will suffer an additional myocardial infarction (MI). In 2010, CAD alone was projected to cost the U.S. $108.9 billion including the cost of health care services, medications, and lost productivity. Cardiovascular diseases claims more lives each year than the next four leading causes of death combined—cancer, chronic lower respiratory diseases, accidents, and diabetes mellitus.

Individuals experiencing symptoms including chest pains, palpitations, and fainting spells, individuals with family histories of heart disease, and individuals of advanced age are typically advised to consult a clinician in order to assess overall heart health, and to diagnose heart disease or the potential for heart disease. A clinician typically performs a physical exam on an individual and asks about personal and family medical history before performing any tests. The clinician may also ask about the individual's lifestyle and habits, and may ask other questions that address known or suspected risk factors associated with heart health. The tests needed to diagnose heart disease can vary depending on the condition the clinician suspects the individual to have, and can include but is not limited to blood tests, chest x-rays, electrocardiograms (ECG), and echocardiograms. More advanced tests or diagnostic techniques can include but is not limited to cardiac catheterization, heart biopsy, cardiac computer tomography (CT) scan, and cardiac magnetic resonance imaging (MRI) scans.

The preliminary and advanced tests can become time consuming, costly and invasive to the individual and results typically need additional time in order for the clinician to review and make a diagnosis based on the results of testing, and together with the data collected from the physical exam and queries, make an assessment of the individual's overall heart health. Communicating the assessment to the individual and communicating changes in the assessment over time can be challenging in that the individual may feel a certain abstraction about an assessment without an understanding of heart health relative to the individual's peer groups, relative to the general population, and/or relative to the individual's own history. Individuals can therefore benefit for improved techniques for communicating heart health with the provider and monitoring heart health over time using a time saving, cost-effective and non-invasive method.

DETAILED DESCRIPTION

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Individuals experiencing symptoms of a heart attack (myocardial infarction) including, but not limited to upper body discomfort in one or both arms, the back, neck, jaw, or stomach, shortness of breath with or before chest discomfort, nausea, vomiting, lightheadedness or fainting, and breaking out in a cold sweat will need to seek immediate medical care and be admitted to the emergency department for diagnosis and treatment.

In transit to the emergency department in response to a chest pain triage situation, emergency medical technicians and clinicians, though maintaining a high knowledge base of medical information, error in that clinician's are human and sometimes may not recognize signs or medical information that suggests the medical condition at hand is a myocardial infarction. Such error in judgment or misinterpretation of medical symptoms may result in increased door to treatment time or possibly patient death.

Emergency medical technicians and clinicians are, therefore, influenced by a number of complex and varied constraints during the decision-making process of how to respond to a patient's medical condition. Clinicians attempt to make informed medical decisions under difficult conditions and it would be an advantage to provide a non-invasive device and method to aid the clinician in providing a quick and accurate medical decision in response to chest pain triage situations. Medical technicians, clinicians and individuals can benefit from accurate assistance to rule-out myocardial infarction in transit to the emergency department where immediate action can be taken to treat the individual upon arrival. Saving time, costs, and most importantly a life.

In the emergency department, the clinician may ask questions associated with suspected risk factors associated with heart health and perform tests needed to diagnose myocardial infarction. These tests can include but is not limited to cardiac markers blood tests, full blood count tests, chest x-rays, echocardiograms, and electrocardiograms (ECG) to diagnosis the patient. Investigation of the ECG waveforms and elevation of specific cardiac markers in serum determines the myocardial infarction as STEMI (ST-segment elevation myocardial infarction) or NSTEMI (Non-ST-segment elevation myocardial infarction).

Complications of diagnosis occur in both STEMI and NSTEMI cases due to similarities in clinical symptoms and signs as there is no difference between NSTEMI and STEMI in clinical presentation. In both cases, patients usually present with similar type of symptoms such as chest pain, nausea and vomiting, sweating, and breathing difficulty. An immediate diagnosis by the clinician is of utmost importance as it determines the individual's course of treatment in the hospital because there is significant risk of death if prolonged. Effective, efficient delivery of treatment is dependent on the timely identification and treatment of MI. Individuals can therefore benefit for improved techniques in providing and communicating results with the clinician using a time saving tool to identify between STEMI and NSTEMI to identify patients that need urgent care so that they can be treated quickly, safely, and cost effectively.

Current clinical practice for treating at risk and/or heart disease patients can include the use of disclosure forms that are filled out by or on behalf of a patient. As noted above, the disclosure forms can be designed to collect information about certain known or suspected heart disease risk factors. The information gathered, along with descriptions of any symptoms that the patient may be experiencing is typically used to obtain a preliminary assessment of the patient's condition. This preliminary assessment can guide the clinician in selecting diagnostics tests to be performed on the patient. The collected data from queries and forms, and diagnostic tests is then used by the clinician to make an assessment of the patient's heart health.

Some embodiments of devices and methods in accordance with the present invention can be used to assist a clinician in making and communicating an assessment of heart health to a patient. Some embodiments of devices and methods in accordance with the present invention can be used to quickly make assessment during chest pain triage situations, monitor and assess heart health over a period of time, and at varying degrees of periodicity.

Figure 1:
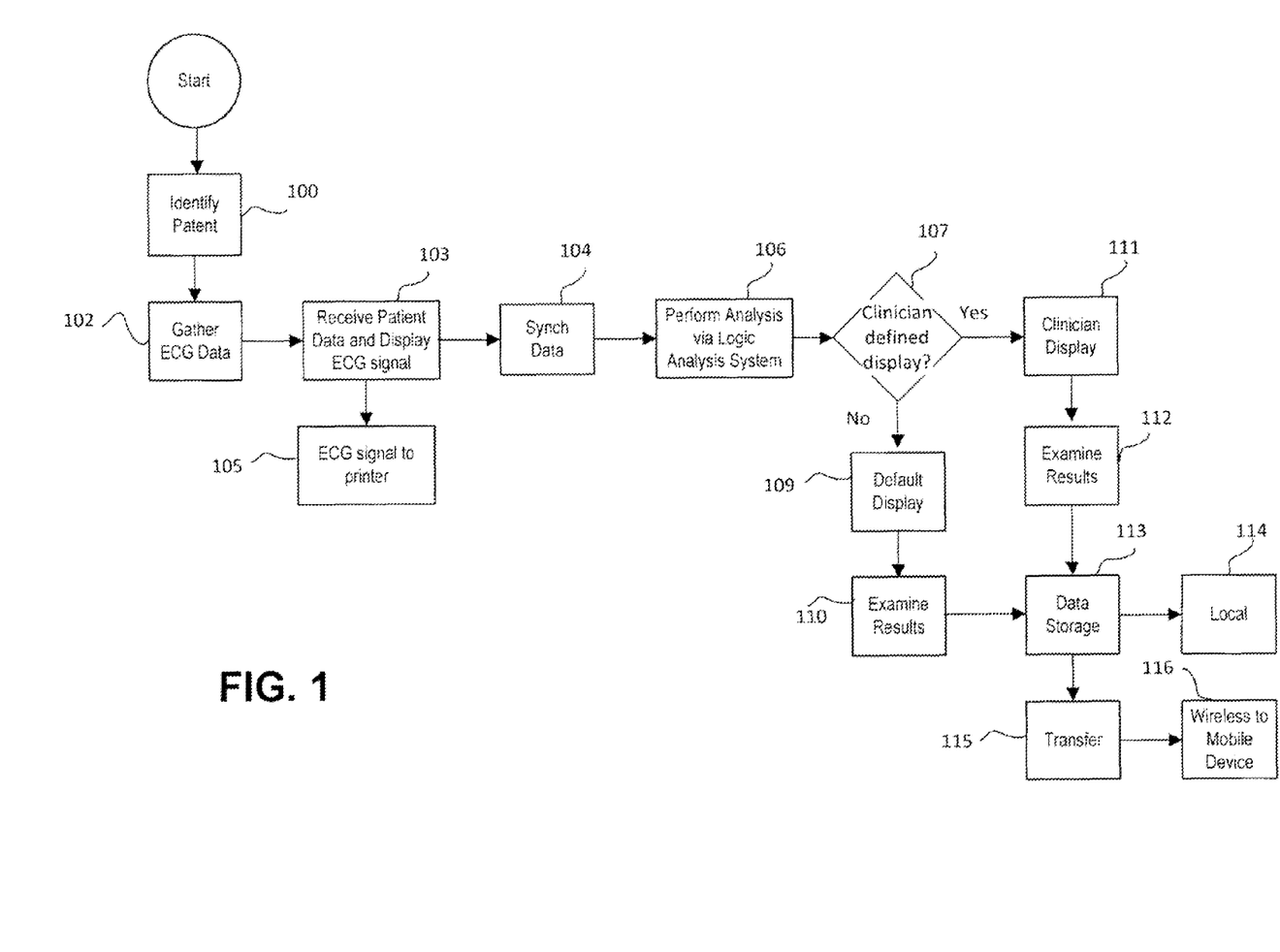
FIG. 1 is a simplified block diagram of a system process, in accordance with an embodiment.

FIG. 1 illustrates a system set-up and method using the system to assist a clinician in making and communicating an assessment of heart health to a patient, in accordance with an embodiment. A patient profile can be created 1) via a third party ECG data acquisition device or 2) directly on a handheld computer device via a manual key-in input method (Step 100). Examples of handheld computer device may include, but are not limited to a laptop, a handheld computer, a tablet, a smartphone, or any other device allowing input and storage of information. An ECG signal can then be collected from the patient (Step 102). The signal data and patient vitals profile can be received (Step 103) and transferred and synchronized (Step 104) with the handheld computer via a suitable data transfer protocol and medium (e.g., a universal serial bus (USB) or RS232 serial port) where the signal can then be displayed on a monitor of the handheld computer device. The clinician can send the ECG signal to print out (Step 105), for example via I/O port or wirelessly via BLUETOOTH® or other wireless methods to communicate with a printer. The received ECG data and patient vital information can then be sent to the Logic Analysis System (Step 106). After analysis a suggestion result is generated on the handheld computer. For results display, clinician can select "Yes" or "No" (Step 107) for default display mode (Step 109) that gives general heart health suggestion result (Step 110) or a custom clinician display (Steps 111 and 112) with focus on specific heart diseases pre-selected by the clinician. Examples may include, but not limited to coronary artery disease (CAD), ischemia, myocardial infarction (MI), etc. Clinician will then have the option to save the examined results (Step 113) either locally on the handheld computer device via hard drive (Step 114), transferred to a mobile device wirelessly via BLUETOOTH® or other wireless methods (Steps 115 and 116), or both. Mobile devices may include a cellular phone. After successful storage of data, system process concludes.

Figure 2:
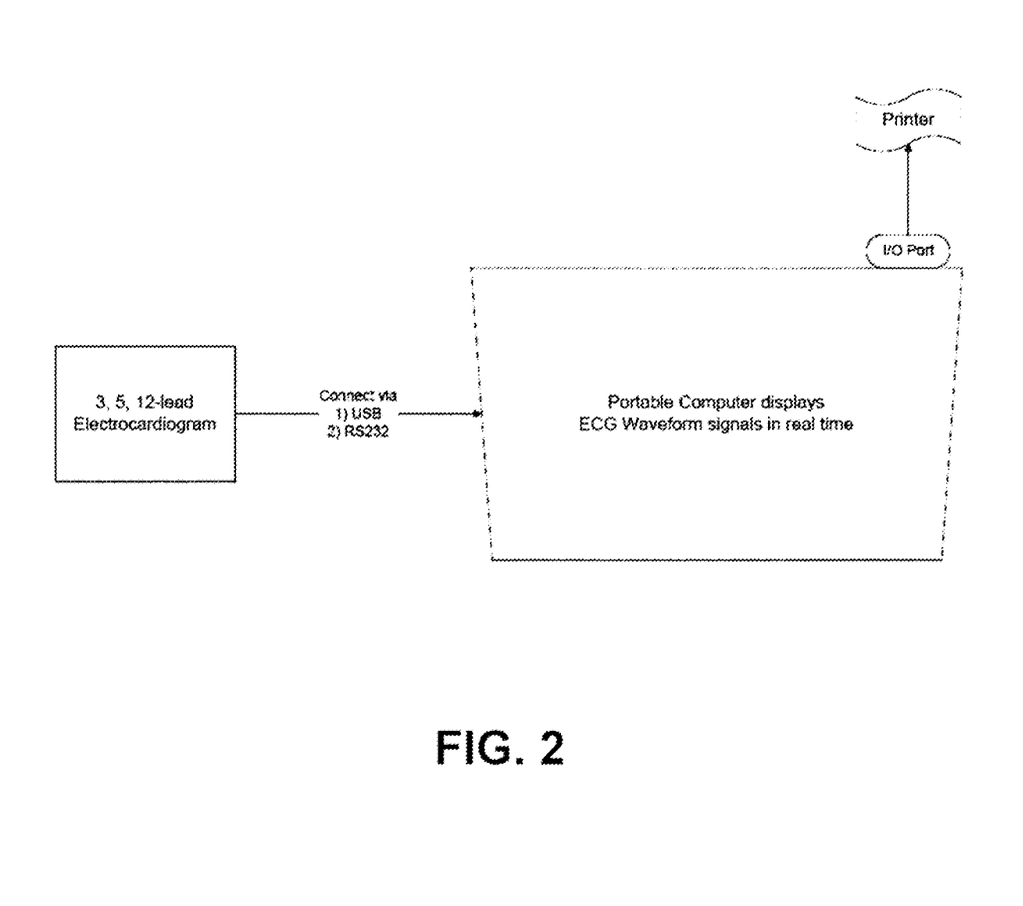
FIG. 2 illustrates an embodiment of a device during synchronize data display of electrocardiogram (ECG) signals collected in real time, in accordance with an embodiment.

FIG. 2 Illustrates examples of third party ECG acquisition devices to include 3, 5, and 12 channel leads to connect via USB or RS232 port with the handheld computer device where waveforms are displayed in real time during data acquisition, in accordance with an embodiment.

Figure 3:
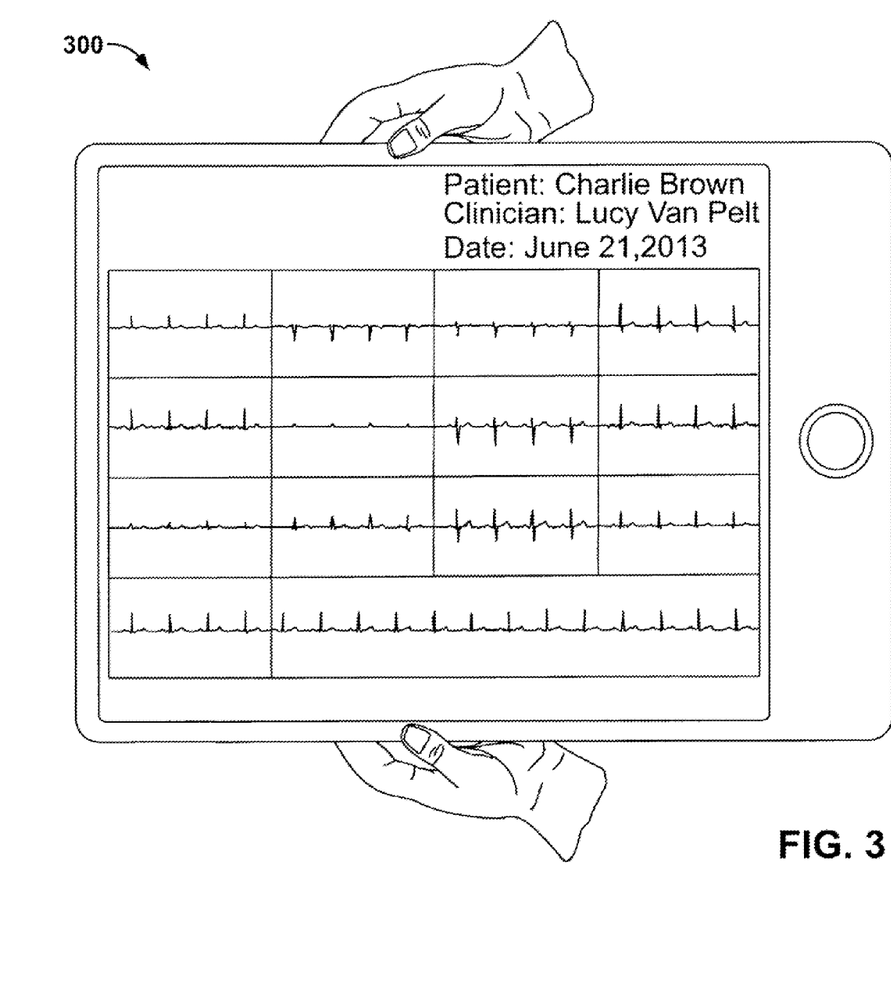
FIG. 3 illustrates an embodiment of a device for monitoring heart health in accordance with the present invention.

FIG. 3 Illustrates an example of a synchronized data display page on the handheld computer device 300 where both patient information and ECG signals are displayed, in accordance with an embodiment.

Figure 4A:
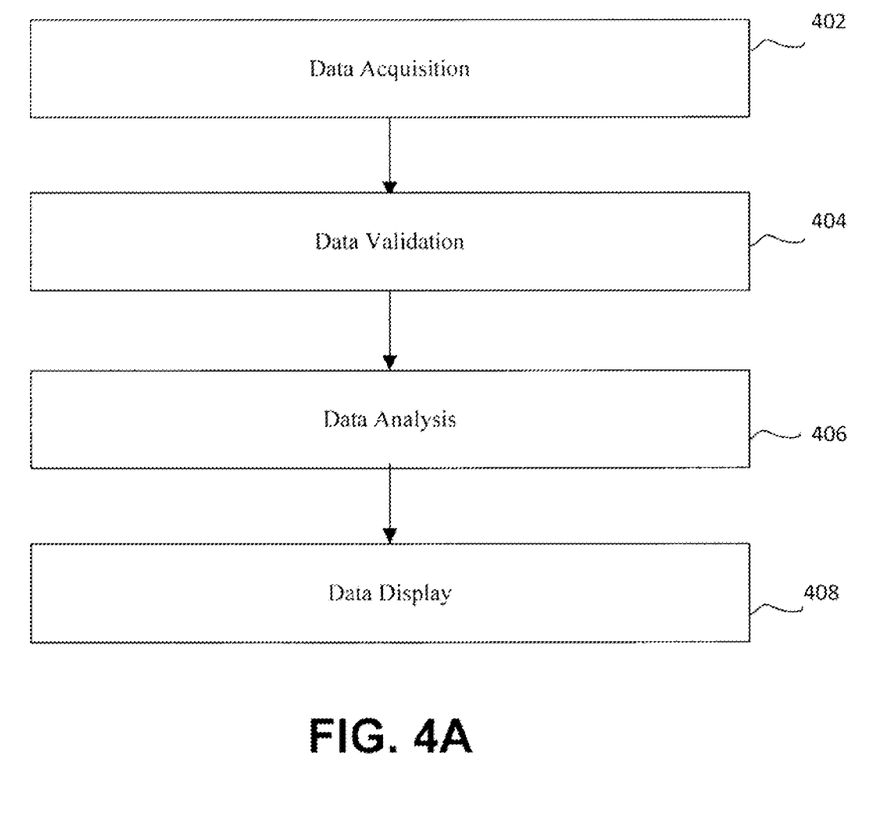
FIG. 4A is a simplified flowchart of the logic analysis process, in accordance with an embodiment.

FIG. 4A is a simplified flowchart for a method of using a logic analysis system that validates and analyzes the acquired ECG signal, together with the patient data and compares against a signal library database, in accordance with an embodiment. Using a statistical analyzer derived from algorithms, the data display result is a probability or likelihood of type(s) of heart disease(s) displayed via a simple infographic report. The method includes data acquisition (Step 402), data validation (Step 404), data analysis (Step 406) and data display (Step 408).

Figure 4B:
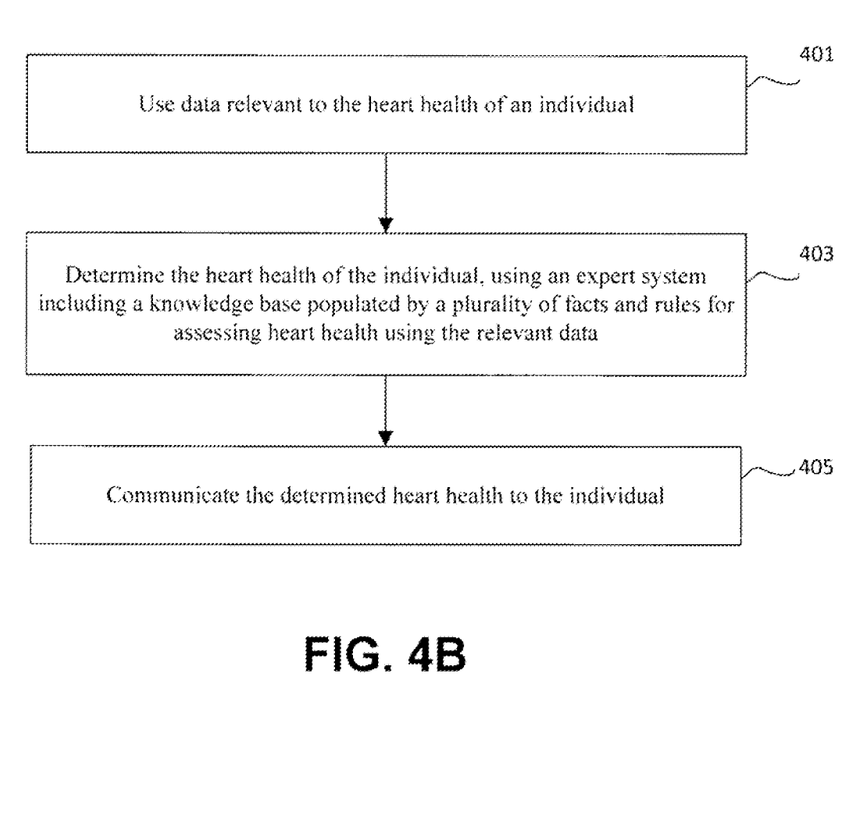
FIG. 4B is a flowchart of an embodiment of a method to assist a clinician in making and communicating an assessment of heart health to a patient, in accordance with an embodiment.

FIG. 4B is a flowchart of an embodiment of a method to assist a clinician in making and communicating an assessment of heart health to a patient, in accordance with an embodiment. The method comprises using data relevant to the heart health of an individual (Step 401) and determining the heart health of the individual, using an expert system including a knowledge base populated by a plurality of facts and rules for assessing heart health using the relevant data (Step 403). At least some of the relevant data can be biographical data and at least some of the relevant data can be measurement data. The heart health can include one or both of an assessment of current health of the individual and a change in heart health that exceeds a threshold. The determined heart health can then be communicated to the individual (Step 405).

Figure 5:
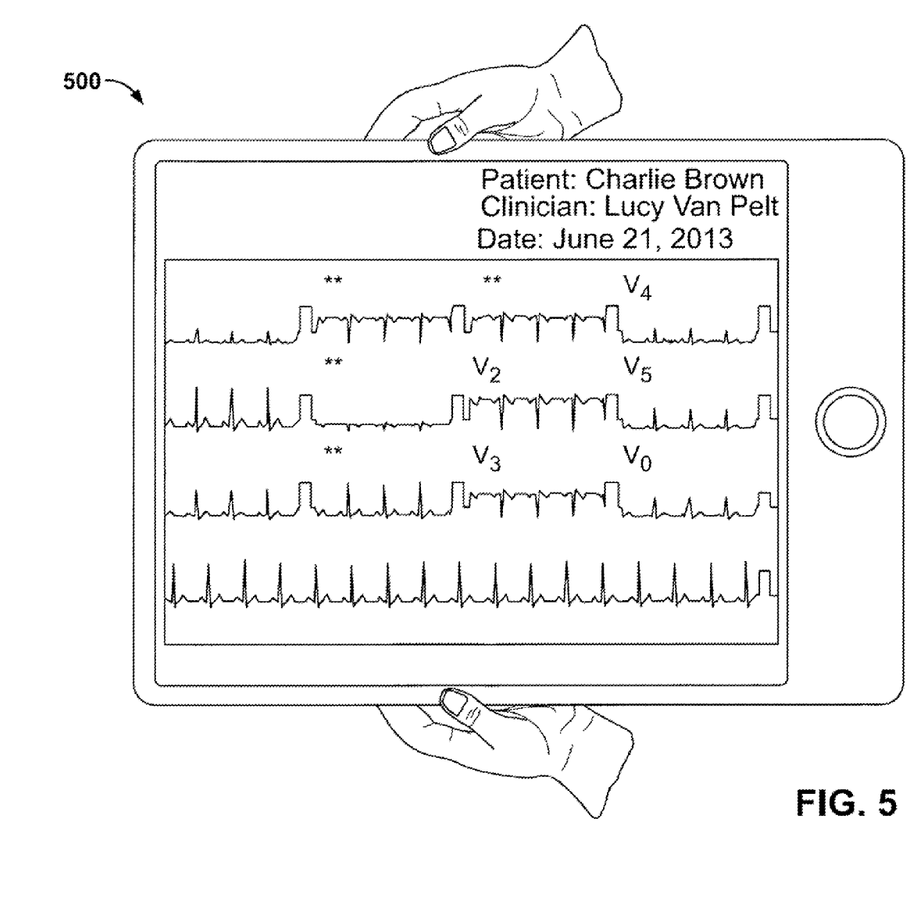
FIG. 5 illustrates an embodiment of a device during the ECG data results display, at which time the clinician can choose to send the ECG signal to a printer for a hard copy print out, in accordance with an embodiment.

FIG. 5 illustrates an embodiment of a device 500 for displaying measurement data, in accordance with an embodiment. As shown, the device can display a 3, 5, or 12-lead channel ECG signals acquired, for example, from a third party data acquisition device via a USB or RS232 serial port connector.

Figure 6A:
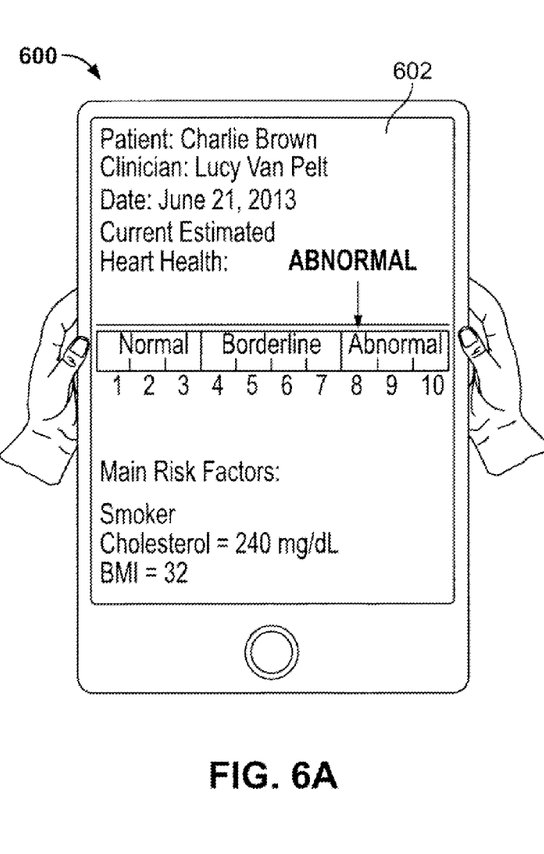
FIG. 6A illustrates an embodiment of a device for assessing general heart health in accordance with the present invention, in accordance with an embodiment.

Referring to FIG. 6A, a device 600 in accordance with an embodiment is shown. The device is a meter that can display a high-level representation of heart health generated from some or all of the data collected. The representation can be a pre-assessment, where the data used to generate the representation comprises only disclosure form data, symptomatic data, and other risk-related data gathered anecdotally from the patient, for example. Alternatively, the representation can be an assessment of heart health, where the data used to generate the representation includes the data of the pre-assessment, and diagnostic data gathered from diagnostic tests. An input device (not shown) can be used to input the data used by the device to generate the representation. The input device can be a keyboard connectable with the meter, a touch screen overlay arranged over a display screen 602 of the device, a separate computer or computing device, an external memory source storing the data (i.e., a flash memory card), etc.

Where the representation displayed by the device is a pre-assessment, the clinician can use the pre-assessment to, for example, explain reasoning for wanting to perform certain diagnostic test(s) or treatments and to validate treatment effectiveness. The pre-assessment can also be used to explain heart health in conjunction with diagnostic data obtained from the diagnostics test(s). Where the representation displayed by the device is an assessment, the clinician can use the assessment to give the patient a high level, best approximation of the patient's past and/or current heart health.

Figure 6B:
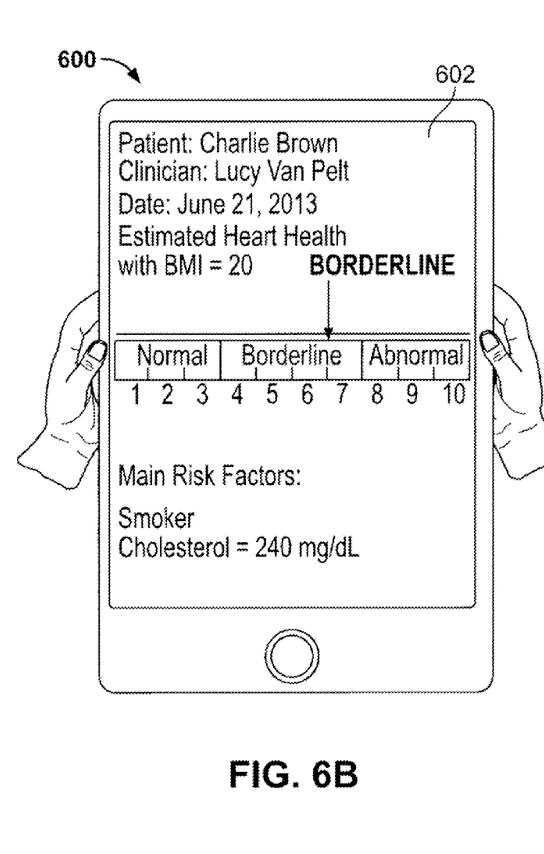
FIG. 6B illustrates the device of FIG. 6A assessing general heart health given a change in one or more risk factors, in accordance with an embodiment.

As shown in FIGS. 6A and 6B, the meter displays a simple color/grayscale gradient marked by ten intervals forming three "zones" of heart health: normal, borderline, and abnormal. An arrow identifies where the patient's heart health falls along the gradient. The number of intervals and zones represented by the gradient is merely exemplary, and can be greater or lesser, depending on the representation that a clinician best feels communicates the heart health to the patient.

Figure 7A:
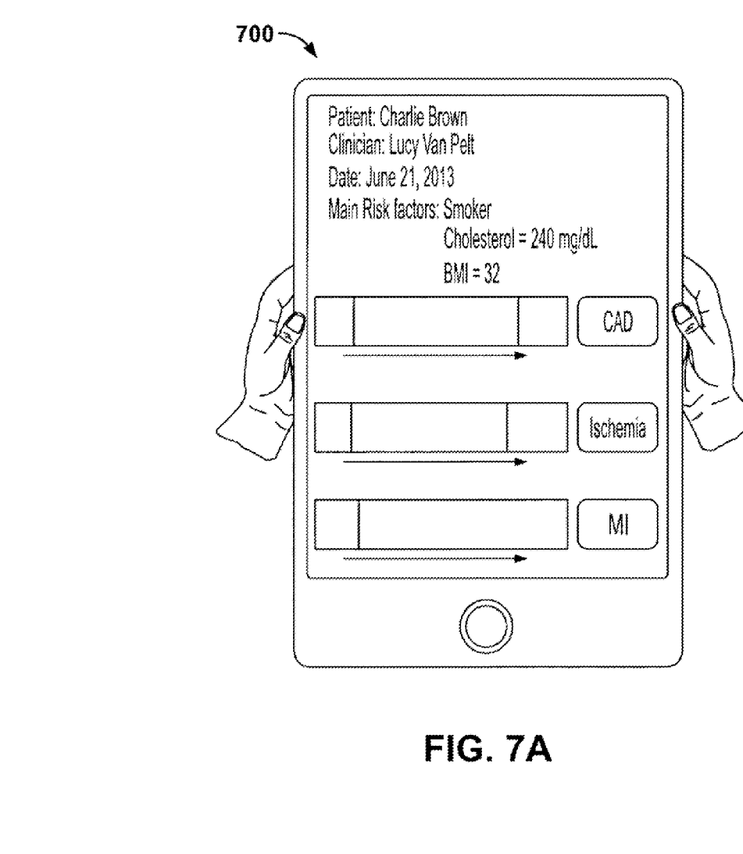
FIGS. 7A-7C illustrates various representations usable with embodiments of devices and methods in accordance with the present inventions for communicating heart health, in accordance with an embodiment.

Referring to FIG. 7A, a device 700 in accordance with an embodiment is shown. A representation displayed on the device can be communicated using a graphical tool pre-selected by the clinician to include various heart diseases, and can include coronary artery disease (CAD), cardiac ischemia, myocardial infarction (MI), and/or other cardiovascular diseases. A simple color/grayscale gradient scale with a horizontal indicator scale of "Low" to "High" represents the individual's probable risk of heart disease. The higher the indicator scale is for a particular heart disease, the higher probability the individual carries for that category. The number of diseases represented by the gradient is merely exemplary, and can be greater or lesser, depending on the representation that a clinician best feels suitable for the environment. For example, in a primary care physician office, disease categories CAD and cardiac ischemia would be recommended in bettering communication of heart health and probable disease risk to the patient.

Figure 7B:
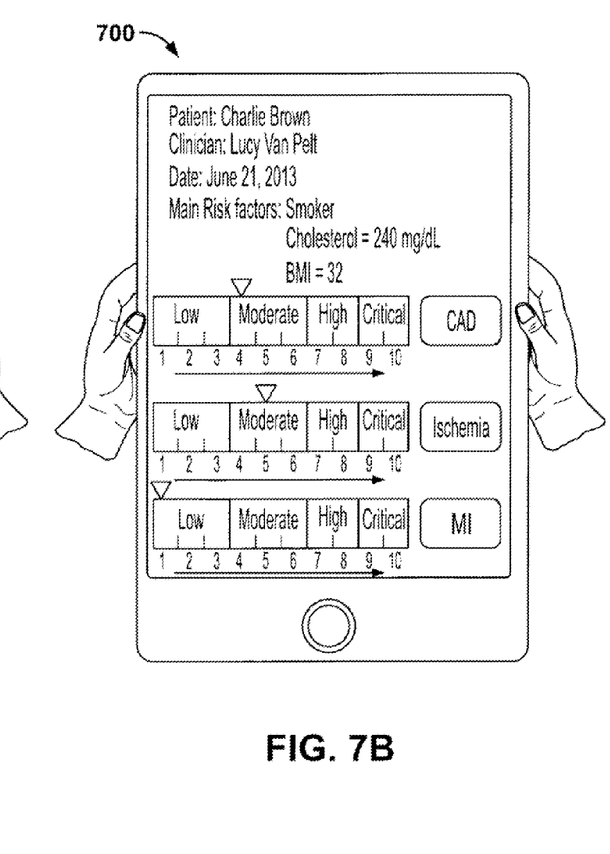

Referring to FIG. 7B, still further, the representation could be communicated using a graphical tool pre-selected by the clinician to include various heart diseases, and can include coronary artery disease (CAD), cardiac ischemia, myocardial infarction (MI), and/or other cardiovascular diseases. A simple color/grayscale gradient marked by ten intervals forming four "zones" of heart disease risk: low, moderate, high, and critical for a specific heart disease category. An arrow identifies where the patient's probable heart disease risk falls along the gradient. The number of intervals and zones represented by the gradient is merely exemplary, and can be greater or lesser, depending on the representation that a clinician best feels communicates the heart disease risk to the patient.

Figure 7C:
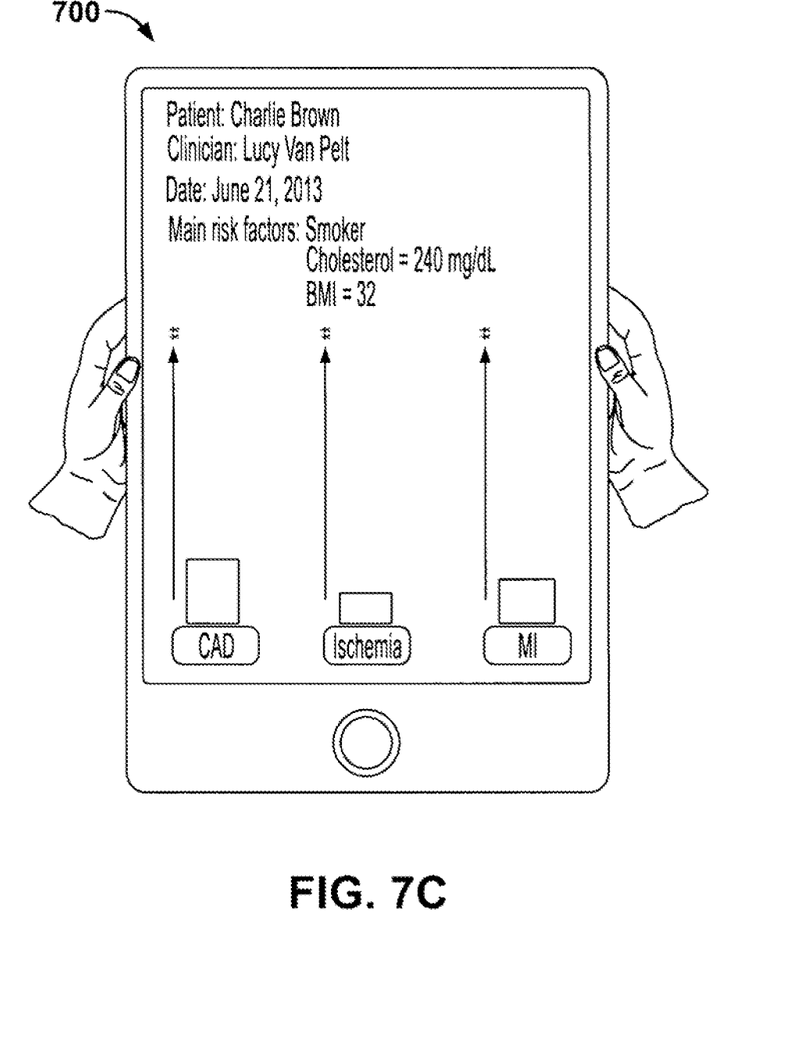

Referring to FIG. 7C, still further, the representation could be communicated using a graphical tool pre-selected by the clinician to include various heart diseases, and can include coronary artery disease (CAD), cardiac ischemia, myocardial infarction (MI), and/or other cardiovascular diseases. A simple color/grayscale gradient scale with a vertical indicator scale of "Low" to "High" represents the individual's probable risk of heart disease. The higher the indicator scale is for a particular heart disease, the higher probability the individual carries for that category.

Figure 8:
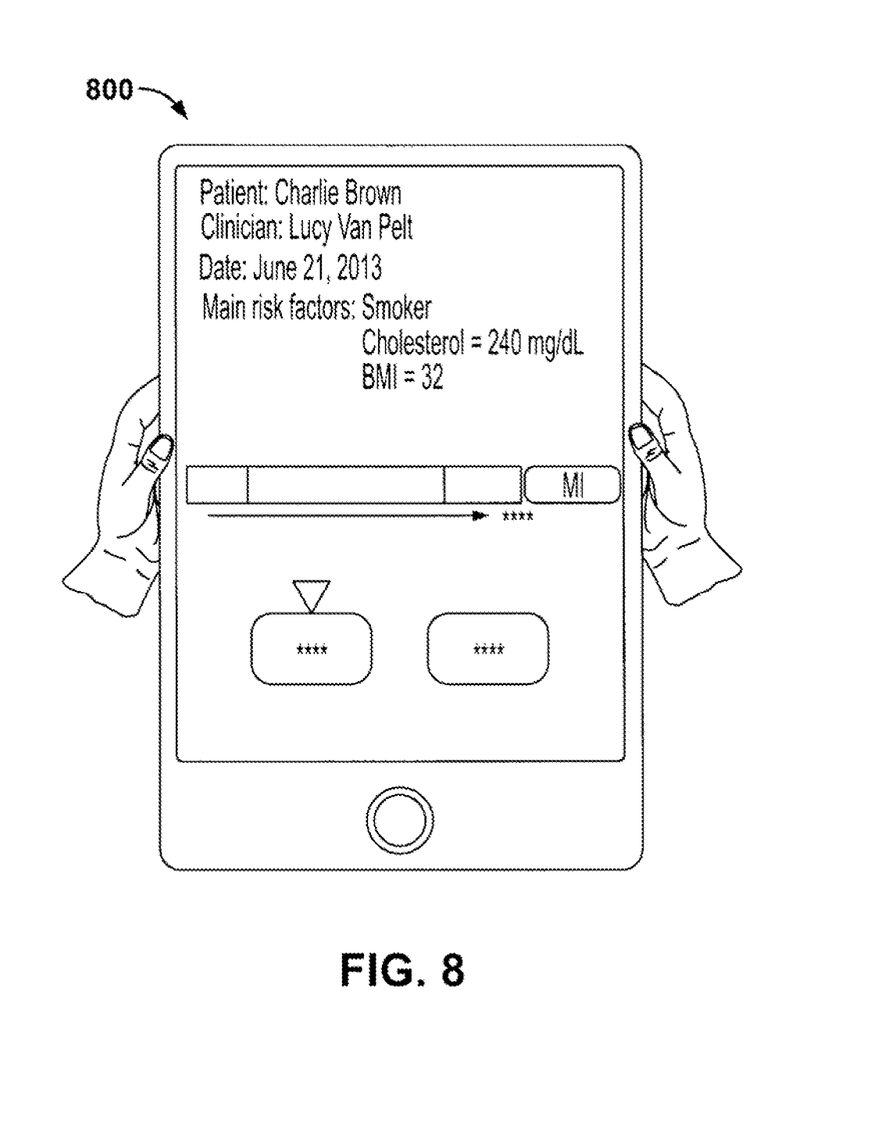
FIG. 8 illustrates details of clinician selection of myocardial infarction (MI) display, in accordance with an embodiment.

Referring to FIG. 8, a device 800 in accordance with an embodiment is shown. A representation on the device of a heart disease myocardial infarction (MI) by the clinician could be used on an ambulatory transportation vehicle, in the emergency department of a hospital, and various other chest triage treatment facilities. The selection of MI further breaks down into STEMI and NSTEMI as determined by the logic analysis system based on input ECG signal and patient vitals data. An arrow identifies the type of MI the patient has. The clear identification of MI to be STEMI or NSTEMI provides a vital tool for the clinician to rapidly and non-invasively respond to an MI situation and take immediate procedures to treat the individual.

Referring to FIGS. 9A-9E, still further, representations displayed on a device need not comprise a gradient, but rather could be communicated using some other graphical tool. For example, the representation can be a skeuomorphic or a metaphoric device, such as a traffic light, a thermometer, a speedometer, an icon representative of a person with cartoonishly exaggerated reaction, emoticons, a heart bar similar to a "life bar" used in video games, and animation, etc.

Figure 9A:
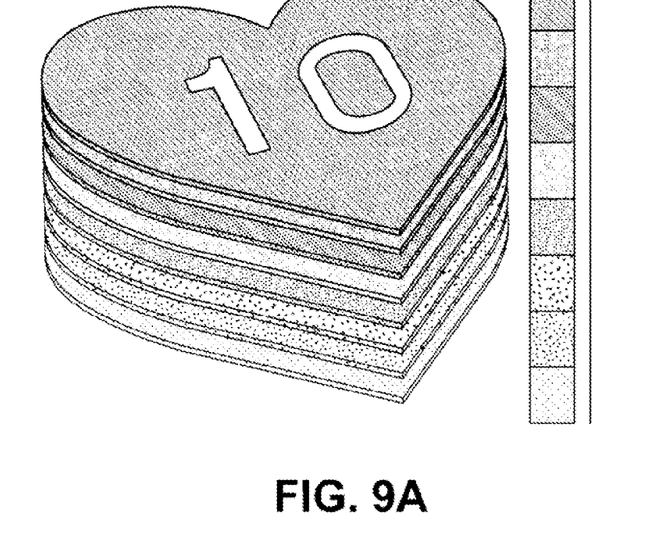
FIG. 9A-9E illustrates various representations usable with embodiments of devices and methods for communicating heart health, in accordance with an embodiment.

Referring to FIG. 9A, a representation is shown comprising a 3D surface graph. Heart health risk displayed through a 3D representation using a heart shaped graph. With each added layer to the heart, the higher the risk level result of the patient. A scale uses a numerical value of 1-10 with each layer represented with a different color, building up progressively from green to red; with "1" representing healthy/normal condition (bottom layer) building up to the top layer "10" representing critical/abnormal condition.

Figure 9B:
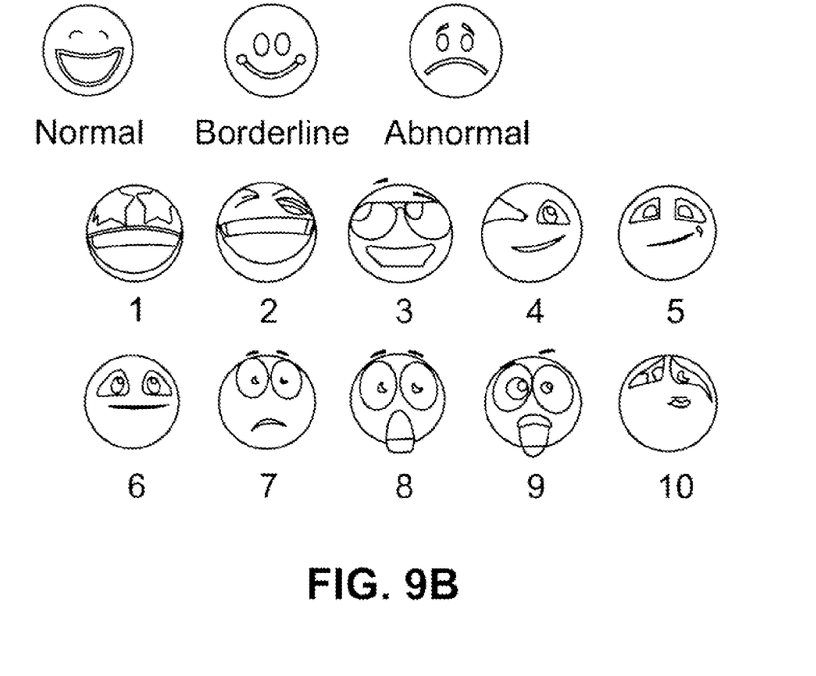

Referring to FIG. 9B, a representation is shown comprising anthropomorphic icons. The icons are assigned recognizable "moods" that correspond to a condition of the patient. The representation can be a simple three tier representation indicating normal (broad smile), borderline (simple smile), and abnormal (frown). The representation can alternatively have a broader range of icon expression as shown in moods ranging from tearful (a "10", representing critical/abnormal condition) to stellar (a "1", representing fit).

Figure 9C:
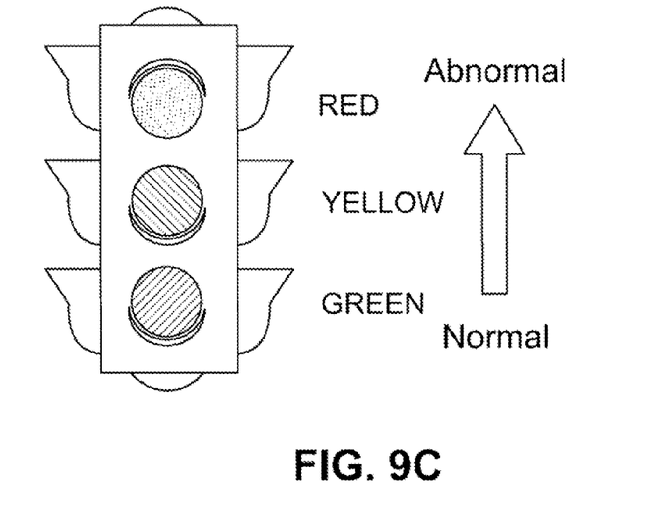

Referring to FIG. 9C, a representation is shown comprising a blinking lights animation. Heart health risk is displayed using green, yellow, and red colored lights. When the result displayed is red, an abnormal condition is indicated. The red light will blink to indicate the patient's heart health is in critical/abnormal condition. The sequence of green, yellow, and red (flashing) lights is not limited to a stop light form. Lights animation can take on any shape or form and follows a sequence of colors resulting in the final color as a flashing/blinking animation.

Figure 9D:
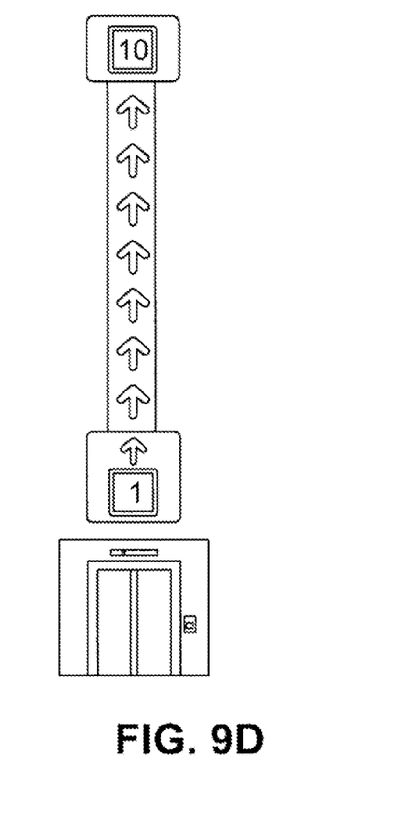
Figure 9E:
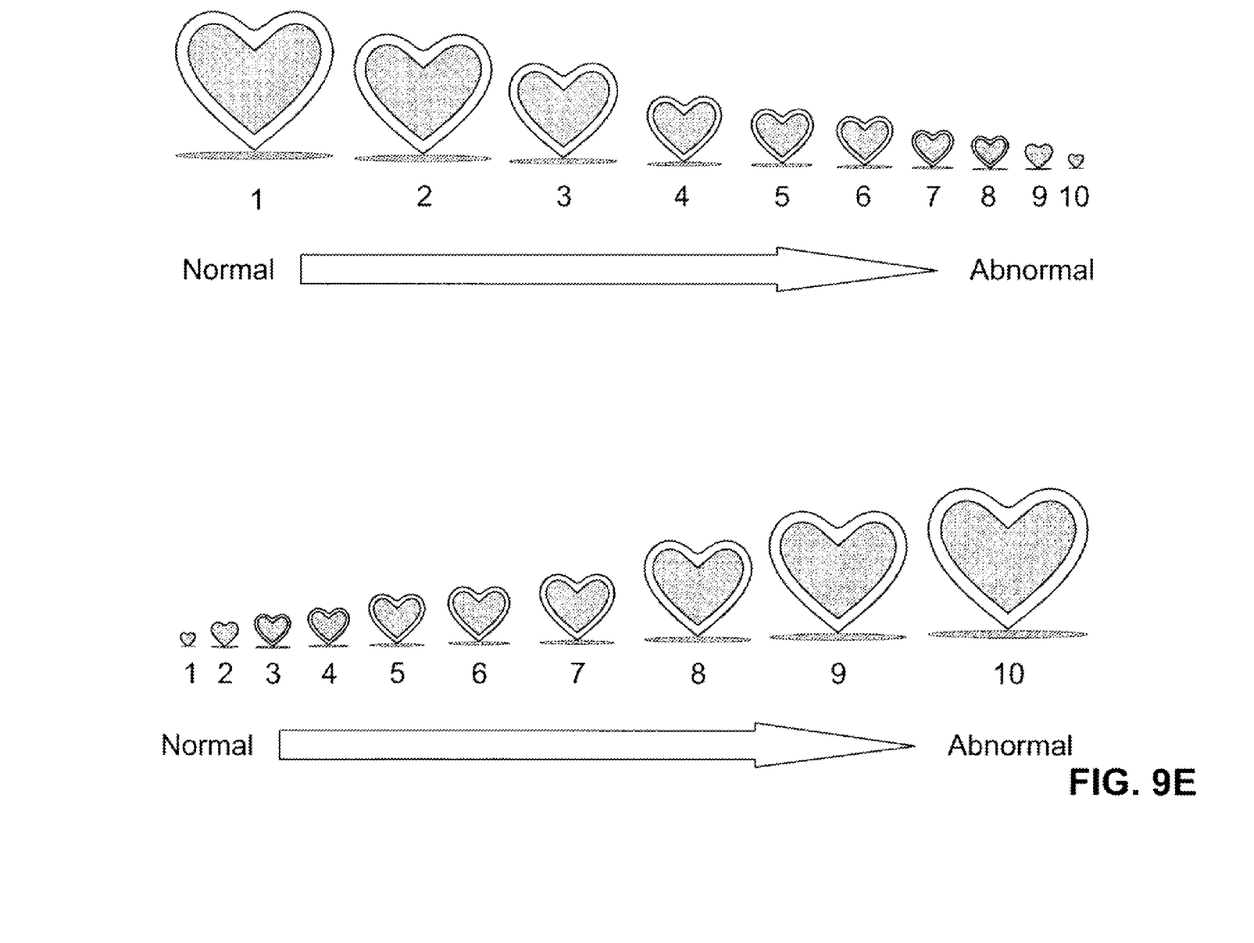

Referring to FIG. 9D, a representation is shown comprising an elevator animation. The animation includes an upwards linear progression of levels 1-10 starting with bottom level=1 to top level=10. The animation will start with elevator doors closing and an up arrow will light up in progression and stop on the "Level" to display patient's heart health test result as a numerical value. A color change of green to red will follow the corresponding number displayed. The progression shown is from NORMAL→ABNORMAL heart health condition Referring to FIG. 9E, a representation is shown comprising a size progression of heart shapes. Heart health risk is displayed using a heart image following a size progression from large to small or from small to large. The scale is a numerical value of 1 to 10, with "1" representing healthy/normal and "10" representing critical/abnormal condition.

One of ordinary skill in the art will appreciate, based on and in light of the teachings provided herein, the myriad different graphical tools that can be used to provide a representation that is a distilled summation communicating the pre-assessment or assessment of heart health. Embodiments described herein are not intended to be limited to any particular iconography or graphical tool. In some embodiments, the clinician or user of the meter can toggle between different representations to better understand the information being delivered.

The wireless transceiver on the handheld computer device can also be used to communicate with a service for monitoring the health of the individual from home or any place where a signal might be transmitted and/or received. It can also communicate the decline in heart health to the individual, either via the graphical display, or by way of an audible signal. This could be useful, for example, in nursing facilities. The device can also periodically send data back to the wearer's clinician for monitoring, either using the wireless transceiver or via the application on the wearer's cellular phone (or other interface device).

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. A system for communicating heart health of an individual to the individual, comprising:
    an input device useable to enter data relevant to the health of the individual;
    wherein at least some of the relevant data are biographical data and at least some of the relevant data are measurement data;
    an expert system including a knowledge base populated by a plurality of facts and rules for assessing heart health;
    wherein the expert system applies the knowledge base to the relevant data to assess heart health; and
    an output device useable to communicate one or both of current heart health of the individual and a change in heart health that exceeds a threshold.

2. The system of claim 1, wherein the system communicates an ischemic heart disease condition of the individual and the output device is useable to communicate one or both of current heart health condition of the individual and a change in ischemic heart disease condition that exceeds a threshold.

3. The system of claim 1, further comprising one electrocardiogram (EKG) data acquisition devices in the form of 3, 5, or 12-lead channel for obtaining vital sign data.

4. The system of claim 1, wherein the biographical data include one or more of age, race, gender, height, weight, medical history, heart disease risk factors, exercise habits and dietary habits.

5. The system of claim 1, wherein the measurement data include one or more of blood pressure measurements, cholesterol measurements, blood test results, chest x-ray results, electrocardiogram (EKG) results, and echocardiogram results.

6. The system of claim 1, wherein the output device is one or both of a display device and a speaker.

7. The system of claim 5, wherein the heart health is communicated via an infographic presented by the display device.

8. The system of claim 1, wherein the output device is further useable to communicate suggestions for the probable risk of specific heart diseases.

9. A method of communicating heart health of an individual to the individual, comprising:
    obtaining data relevant to the heart health of the individual;
    wherein at least some of the relevant data are biographical data and at least some of the relevant data are measurement data;
    using an expert system including a knowledge base populated by a plurality of facts and rules;
    assessing the heart health of the individual by applying, using the expert system, the knowledge base to the relevant data;
    wherein the heart health includes one or both of an assessment of current health of the individual and a change in heart health that exceeds a threshold; and
    communicating the determined heart health to the individual.

10. A non-transitory computer readable storage medium, including instructions stored thereon which when read and executed by one or more computers cause the one or more computers to perform the steps comprising:
    obtaining data relevant to the heart health of the individual;
    wherein at least some of the relevant data are biographical data and at least some of the relevant data are measurement data;
    using an expert system including a knowledge base populated by a plurality of facts and rules;
    assessing the heart health of the individual by applying, using the expert system, the knowledge base to the relevant data;
    wherein the heart health includes one or both of an assessment of current health of the individual and a change in heart health that exceeds a threshold; and
    communicating the determined heart health to the individual.

11. The system of claim 1, wherein the output device is configurable to pre-select conditions related to heart health that are communicated by the output device.

12. The system of claim 1, further comprising a logic analysis system, and wherein the logic analysis system includes the expert system, and wherein the logic analysis system validates the relevant data prior to the expert system applying the knowledge base to the relevant data.

13. The system of claim 1, further comprising a signal library database;

wherein the relevant data includes an electrocardiogram; and wherein the expert system assesses the heart health of the individual via a statistical comparison of the electrocardiogram to the signal library database.

14. The system of claim 1, wherein the relevant data includes an electrocardiogram; and wherein the system determines based on the electrocardiogram whether a myocardial infarction is present and where present communicates, via the output device, whether the myocardial infarction is an ST-segment elevation myocardial infarction (STEMI) or a non-ST-segment elevation myocardial infarction (NSTEMI).

15. The system of claim 1, wherein the assessment of heart health by the expert system is a pre-assessment; and wherein the expert system further determines one or more recommended follow-on diagnostic tests or treatments; and wherein the output device is further useable to communicate the one or more recommended follow-on diagnostic tests or treatments.

16. The method of claim 9, wherein the determined heart health to the individual is communicated via a display and further comprising:

configuring the display by pre-selecting conditions related to heart health that are communicated by the display.

17. The method of claim 9, wherein the expert system is part of a logic analysis system, and further comprising:

validating the relevant data, using the logic analysis system, prior to the expert system applying the knowledge base to the relevant data.

18. The method of claim 9, wherein the relevant data includes an electrocardiogram; and wherein assessing the heart health of the individual includes applying a statistical comparison of the electrocardiogram to a signal library database.

19. The method of claim 9, wherein the relevant data includes an electrocardiogram; and further comprising:

determining based on the electrocardiogram whether a myocardial infarction is present and where present communicating, via the output device, whether the myocardial infarction is an ST-segment elevation myocardial infarction (STEMI) or a non-ST-segment elevation myocardial infarction (NSTEMI).

20. The method of claim 9, wherein the assessment of heart health by the expert system is a pre-assessment; and further comprising:

determining, via the expert system, one or more recommended follow-on diagnostic tests or treatments; and communicating the one or more recommended follow-on diagnostic tests or treatments.

\* \* \* \* \*